United States Patent [19]

Nakane

[11] Patent Number: 5,021,079
[45] Date of Patent: Jun. 4, 1991

[54] SODIUM CHLORIDE IN NOVEL CRYSTAL FORM AND AQUEOUS SOLUTION CONTAINING THE SAME

[75] Inventor: Shigeru Nakane, Yokohama, Japan

[73] Assignee: Techno-Bio Co., Ltd., Tokyo, Japan

[21] Appl. No.: 363,733

[22] Filed: Jun. 9, 1989

[30] Foreign Application Priority Data

Jun. 21, 1988 [JP] Japan .............................. 63-151262

[51] Int. Cl.$^5$ ..................... A01N 3/02; C01D 3/24; C01D 3/04; C09K 19/04
[52] U.S. Cl. ......................... 71/68; 423/499; 23/303; 252/299.01
[58] Field of Search ............. 423/499, 263; 23/303, 23/159; 252/299.01; 71/68

[56] References Cited

U.S. PATENT DOCUMENTS 4,061,557 12/1977 Nishizawa et al. .................. 204/277

FOREIGN PATENT DOCUMENTS 25092 6/1911 United Kingdom .
848328 9/1960 United Kingdom .

OTHER PUBLICATIONS

Tarjan et al, "Laboratory Manual on Crystal Growth", 1972, pp. 64–70.
Maruyama et al, Journal of Crystal Growth, vol. 62, 1983, pp. 401–408.

*Primary Examiner*—Richard L. Raymond
*Assistant Examiner*—B. Bembenick
*Attorney, Agent, or Firm*—Armstrong, Nikaido, Marmelstein, Kubovcik & Murray

[57] ABSTRACT

Sodium chloride in a flat tetrahedronal crystal form and an aqueous solution containing (i) sodium chloride in a flat tetrahedronal crystal form or sodium chloride capable of converting to a flat tetrahedronal crystal form and (ii) iron chloride.

4 Claims, 3 Drawing Sheets

SODIUM CHLORIDE IN NOVEL CRYSTAL FORM AND AQUEOUS SOLUTION CONTAINING THE SAME

BACKGROUND OF THE INVENTION

1. Field of the Invention

The present invention relates to sodium chloride having a novel crystal form and to an aqueous solution containing sodium chloride of that novel crystal form or able to convert to that novel crystal form.

2. Description of the Related Art

The crystal of sodium chloride has a rock salt structure and, as a crystal form, there are generally known cubes and cubic hexahedrons (tetradecahedrons).

SUMMARY OF THE INVENTION

An object of the present invention is to provide sodium chloride having a novel crystal form.

Another object of the present invention is to provide an aqueous solution containing sodium chloride having the above-mentioned novel crystal form or able to convert to this crystal form, and iron chloride.

Other objects and advantages of the present invention will be apparent from the following description.

In accordance with the present invention, there is provided sodium chloride in a flat tetrahedronal crystal form.

In accordance with the present invention, there is also provided an aqueous solution containing (i) sodium chloride in a flat tetrahedronal crystal form or sodium chloride capable of converting to a flat tetrahedronal crystal form and (ii) iron chloride.

BRIEF DESCRIPTION OF THE DRAWINGS

The present invention will be better understood from the description set forth below with reference to the accompanying drawings, in which.

DESCRIPTION OF THE PREFERRED EMBODIMENTS

The present inventor engaged in long years of research and as a result succeeded in the manufacture of sodium chloride having a unique crystal form unknown in the prior art. Further, the present inventor discovered that sodium chloride having this unique crystal form displays the action of improving the chemical stability of skin ointments and suppresses secondary effects. Further, the present inventor discovered that an aqueous solution of sodium chloride having this novel crystal form or sodium chloride able to convert to this crystal form, and iron chloride has an unexpected effect of promoting activity. This activity promoting action means, for life, a positive effect on the maintenance of life and, for nonlife, the nature of strengthening the inherent characteristics of a substance and thus a positive effect on, for example, energy conversion action.

Figure 1:
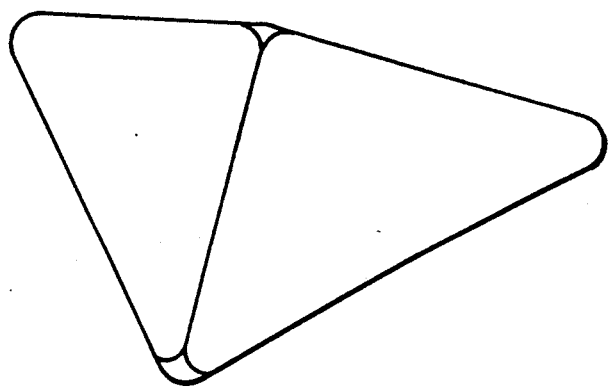
FIG. 1 is a perspective view of the sodium chloride of the relatively small flat tetrahedronal crystal form according to the present invention.
Figure 2:
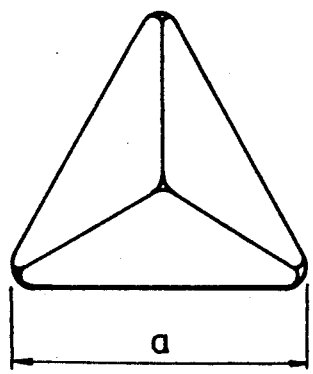
FIG. 2 is a plan view of the crystal of FIG. 1.
Figure 3:
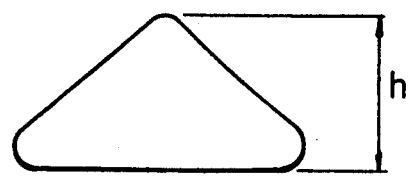
FIG. 3 is a front view of the crystal of FIG. 1.
Figure 4:
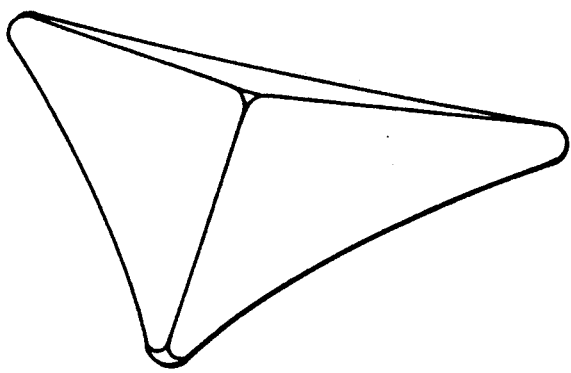
FIG. 4 is a perspective view of sodium chloride of the relatively large flat tetrahedronal crystal form according to the present invention.
Figure 5:
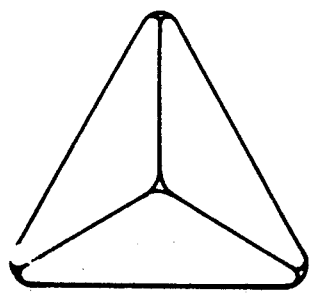
FIG. 5 is a plan view of the crystal of FIG. 4.
Figure 6:
FIG. 6 is a front view of the crystal of FIG. 4.

The novel crystal form shown by the sodium chloride of the present invention, briefly speaking and as shown in FIGS. 1 to 3, is a flat tetrahedron comprised of a regular tetrahedron with one height reduced. More precisely speaking, it is formed from three side faces of substantially the same isosceles triangles (however, the equal sides being shorter than the base) and one bottom face of a roughly equilateral triangle with the four vertexes being slightly rounded. The degree of flatness of the crystal of the present invention varies over a wide range and in general the degree of flatness advances as the dimensions of the crystal become larger. Here, if the degree of flatness is shown by the length a of one side of the equilateral triangle base (see FIG. 2) and the shortest height h of the flat tetrahedron (see FIG. 3), in general, a:h is 1:0.8 to 50:1. In a relatively small crystal (for example, one where one side a of the equilateral triangle base is about 0.05 mm), a:h is 1:0.8 to 5:1. In a relatively large crystal (for example, one where the one side a is about 1 mm), a:h becomes 5:1 to 10:1. If the crystal grows further and the one side a becomes about 1.5 mm or more, then, as shown in FIGS. 4 to 6, the degree of flatness further advances and a:h becomes 5:1 to 50:1 and further the central region of the base becomes depressed and therefore the three vertexes of the base stick out in form.

Therefore, the term "flat tetrahedron" is used herein as a term expressing all of the above shapes explained along with the above FIGS. 1 to 6.

The dimensions of the sodium chloride of the flat tetrahedronal crystal form of the present invention vary over a wide range depending on the crystallization conditions, but in general are about 0.05 to 3 mm.

The sodium chloride in the flat tetrahedronal crystal form of the present invention, for example, may be manufactured by treating an aqueous solution of sodium chloride with a unique catalyst discovered by the present inventor (that is, a flat tetrahedronal crystal form imparting catalyst, hereinafter sometimes referred to simply as "the catalyst").

The above-mentioned catalyst may be manufactured, for example, as follows:

Iron chloride, for example, ferric chloride, is added to an aqueous solution obtained by treating cristobalite with an aqueous mineral acid (for example, a hydrohalogenic acid, preferably hydrochloric acid). When this solution is left standing for a long period (for example, 1 to 24 hours), a solution with a light brown color is obtained. This solution is referred to below as solution I. Solution I is diluted with a large volume (for example, $10^2$ to $10^4$ fold) of distilled water and again allowed to stand for a long period. Next, a saccharide, for example, sucrose (white sugar, granular sugar, etc.) is added, then the solution allowed to stand for a further long period, whereupon a solution of a light yellow color is obtained. This is referred to below as solution II.

On the other hand, a small amount (for example, 0.1 to 5%) of iron chloride, for example, ferric chloride, is added to an aqueous solution of sodium bichromate at close to saturation (for example, 100 ml of water in which about 300 g of sodium bichromate dihydrate is dissolved) and the solution is allowed to stand for a long period, then a solution with the insoluble components removed is prepared. Here, use may be made of potassium bichromate or potassium permanganate instead of sodium bichromate. To this solution is added ¼ to ¾ volumes of the above-mentioned solution II. This is allowed to stand for a long period and then heated (for example, 60° C. to 80° C.), whereupon a caramel-like solid is product. This is washed with water, whereupon the desired flat tetrahedronal crystal form imparting catalyst is obtained in the form of a granular solid of a black-brown color.

The sodium chloride having the unique crystal form of the present invention may be manufactured by treating in the following way an aqueous solution of sodium chloride using the above-mentioned catalyst.

First, a concentrated aqueous solution of sodium chloride is prepared. As the sodium chloride, use may be made of various types of salt (for example, rock salt, crude salt, culinary salt, table salt.) Seawater may also be concentrated and used as the aqueous solution of sodium chloride. The concentration of sodium chloride of the aqueous solution of sodium chloride is preferably 25% or more. 0.01 to 1% by weight of the above-mentioned catalyst is added to the above-mentioned concentrated aqueous solution of sodium chloride, then the solution is evaporated to dryness. Next, distilled water is added to the solid resulting from the evaporation to dryness so as to dissolve the same, then the solution again evaporated to dryness. This operation is repeated several times. Finally, distilled water is added to the solid resulting from the evaporation to dryness, then the catalyst is filtered out and the filtrate is evaporated to dryness, whereupon the desired sodium chloride crystals of the flat tetrahedronal crystal form are obtained together with cubical crystals and cubic hexahedronal crystals (below, sometimes referred to simply as cubical crystals). The ratio of volume of the obtained flat tetrahedronal crystals and the cubical crystals, etc. differs depending on the crystallization conditions, but in general the ratio of the flat tetrahedronal crystals to the cubical crystals, etc. is 1:100 to 1:3.

The cubical crystals, etc. obtained together with the above-mentioned flat tetrahedronal crystal form alone are collected, dissolved in distilled water, and recrystallized, whereupon in addition to the cubic crystals, etc., the same flat tetrahedronal crystals as mentioned above are generated. Further, for example, the cubical crystals obtained at this stage alone are collected and similarly recrystallized, whereupon again flat tetrahedronal crystals are generated together with the cubical crystals, etc. Subsequently, the same operation is repeated, whereupon flat tetrahedronal crystals are partially generated. That is, sodium chloride treated by the above-mentioned flat tetrahedronal crystal form imparting catalyst, even if the crystal form is for example cubical and cubic hexahedronal, can convert to the flat tetrahedronal crystal form upon several repetitions of normal recrystallization. In the present specification, "sodium chloride with convertibility to flat tetrahedronal crystal form" means the ability to convert to a flat tetrahedronal crystal by repeated recrystallization since the actual crystal form is a cube or cubic hexahedron, but treatment by the flat tetrahedronal crystal form imparting catalyst has already been undergone.

Conversely, when just the flat tetrahedronal crystals are collected and similarly recrystallized, not only flat tetrahedronal crystals but also cubical crystals, etc. are produced. These cubical crystals, etc. may also be once again converted to flat tetrahedronal crystals by recrystallization, so are included in the above-mentioned "sodium chloride with convertibility to flat tetrahedronal crystal form".

The flat tetrahedronal crystals according to the present invention have the effect of suppressing the secondary effects of skin ointments and improving chemical stability. The above-mentioned skin ointments are, for example, cream emulsions for the treatment of acne vulgaris, in particular cream emulsions for the treatment of acne vulgaris containing vitamin A acid (tretinoin). A cream emulsion containing vitamin A acid generally comprises active ingredients of vitamin A acid and also water repelling substances (liquid and solid fatty acids, aliphatic alcohol, fatty acid esters, waxes and hydrocarbons tolerable as medicines), nonionic emulsifiers, preservatives, antioxidants, and water and further small amounts of other additives (for example, moisturizers, metallic ion sealants, paints, perfumes, sunlight blockers, local corticosteroids). If the flat tetrahedronal crystal sodium chloride of the present invention is added to such vitamin A acid containing cream emulsions in amounts of 0.2% to 10% by weight, preferably 0.3 to 1% by weight, there is no adverse effect on the pharmacological action of the active ingredient, vitamin A acid, and the secondary effects of the above-mentioned cream emulsions (for example, spots, stinging, itchiness) are remarkably suppressed and, further, the chemical stability to ultraviolet rays, etc. is improved.

Further, if the sodium chloride of a flat tetrahedronal crystal form according to the present invention is used compounded with a salt of a metal element, for example, inorganic salts or organic salts of lithium, potassium, magnesium, calcium, vanadium, chrome, manganese, iron, strontium, cobalt, nickel, molybdenum, cadmium, ..aluminum, copper, etc. or with carbon or silicon, a deodorizing effect or water purification effect is exhibited. Further, there are a preservative and rust preventing effect, a freshness maintaining effect for animal and vegetable matter, an antipathogenic bacteria effect, an effect of promotion of antigens and antibodies, a cancer suppressing effect, a suppressive effect on static electricity damage, and a soil and oil improving and vegetable growth promoting effect.

An aqueous solution containing at least one of the sodium chloride of a flat tetrahedronal crystal form according to the present invention and the above-mentioned sodium chloride with convertibility to the flat tetrahedronal crystal form (the two together being sometimes referred to below as "unique crystal sodium chloride") together with iron chloride, for example, ferric chloride displays an activity promoting action.

The composition of the above-mentioned aqueous solution generally is: 2500 to $25 \times 10^8$ parts by weight of an iron chloride compound, preferably $2 \times 10^5$ to $5 \times 10^5$ parts by weight, further preferably $23 \times 10^4$ to $25 \times 10^4$ parts by weight, to one part by weight of the unique crystal sodium chloride. If the amount of the iron chloride compound becomes less than 2500 parts by weight, the activity promoting action disappears. Further, if it exceeds $25 \times 10^8$ parts by weight, the activity promoting effect disappears. Further, the amount of water is $10^6$ to $10^{20}$ parts by weight, preferably $10^8$ to $10^{18}$ parts by weight, more preferably $10^{10}$ to $10^{16}$ parts by weight with respect to one part by weight of the total of the unique crystal sodium chloride and the iron chloride compound. If the dilution by water is less than $10^6$ fold, the activity promoting effect disappears and if over $10^{20}$ fold, the activity promoting effect disappears.

However, when preparing the aqueous solution in actuality, the method of dissolving the unique crystal sodium chloride and iron chloride compound together in distilled water is not suitable. The unique crystal sodium chloride is dissolved in distilled water and this solution is further diluted two or more times with distilled water so as to prepare a dilute aqueous solution of unique crystal sodium chloride. Into this dilute aqueous solution may be dissolved the necessary amount of iron chloride compound to prepare the solution.

When treating fuel (for example, coal) by the above-mentioned aqueous solution according to the present invention, the coal is improved in combustion performance compared with untreated coal. Further, in iron reinforcement, the rust prevention effect is assisted. The aqueous solution of the present invention acts to maintain life (for example, prolong and preserve the life of small earthworms) and acts to maintain the freshness of vegetable matter (for example, cut flowers).

EXAMPLES

The present invention will now be further illustrated by, but is by no means limited to, the following Examples.

EXAMPLE 1

Ten grams of gray cristobalite (produced by Higashi Toru-Mura, Shimokita-gun, Aomori-ken, Japan) was pulverized, charged into 100 ml of 0.5 NHCl, and agitated. The solution was heated on a water bath at about 60° C. for 5 hours, then filtered by filter paper to remove the insoluble components. To the obtained solution was added and mixed in to dissolve enough ferric chloride ($FeCl_3.6H_2O$) to a percentage of about 24% by weight. This mixed solution was allowed to stand at ordinary temperature for one night. In this way, a solution I having a light brown color was obtained. Next, this solution I was diluted $10^3$ fold with water and allowed to stand at ordinary temperature for one night. Next, 30 grams of white sugar was added to 120 ml of the obtained solution. The solution was agitated and then allowed to stand at ordinary temperature for one night. In this way, the solution II with a light yellow color was obtained.

On the other hand, 300 grams of sodium bichromate dihydrate ($Na_2Cr_2O_7$) was added to 100 ml of water and agitated to prepare a concentrated aqueous solution of sodium bichromate. To this concentrated aqueous solution of sodium bichromate was added ferric chloride ($FeCl_3.6H_2O$) to an amount of about 0.1% w/v. The solution was agitated, then allowed to stand at ordinary temperature over night, then filtered with filter paper to remove the insoluble components. The liquid obtained in this way was placed in a beaker, solution II was added so that the amount of said solution II was one part by volume to two parts by volume of the liquid, the solution was agitated, then it was allowed to stand at ordinary temperature for 12 hours. This is placed in a thermostat and warmed at about 70° C. for about 1 hour. The thus produced caramel-like substance was washed with water to obtain the insoluble solids. The solids were dried, whereupon a granular flat tetrahedronal crystal form imparting catalyst with a black-brown color was obtained.

Figure 7:
FIG. 7 and FIG. 8 are photographs in place of drawings showing the structure of the crystal according to the present invention.
Figure 8:
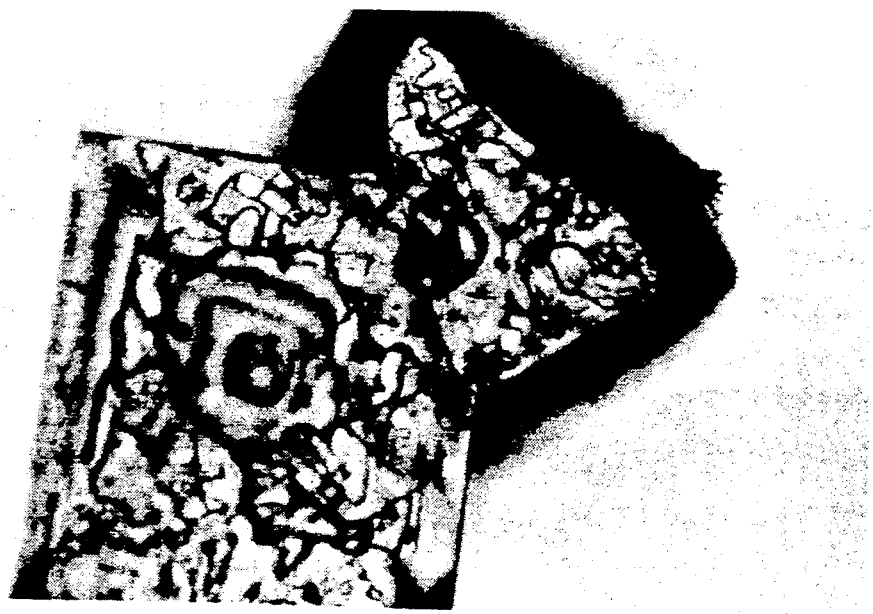

Next, seawater was filtered and concentrated to prepare a concentrated aqueous solution. The above-mentioned catalyst was added to the above concentrated aqueous solution for a ratio of 0.5% by weight w/w, the solution agitated, and the solution gradually evaporated to dryness on a water bath. After the evaporation to dryness, further distilled water was added and simultaneously the solution was evaporated to dryness. This operation was repeated a total of 5 times. Next, the product was dissolved in distilled water, the catalyst filtered out, and the filtrate evaporated again on a water bath, whereupon flat tetrahedronal crystals and cubical crystals were obtained at a ratio of about 1:5. FIG. 7 and FIG. 8 are electron micrographs (each 100 magnifications) of the crystal produced. The crystal shown in FIG. 8 precipitated in a form with the flat tetrahedronal crystals and cubical crystals fused.

Just the flat tetrahedronal crystals were collected and analyzed, whereupon it was found that the melting point was 799° C. Elemental analysis gave the following results:

| Cl: 55.4, | Na: 35.4, | Mg: 0.54, |
|---|---|---|
| Br: 0.05, | S: 0.5, | Ca: 0.05, |
| K: 0.05, | Sr: 0.01, | Others: 8.0. |

Further, crystals with convertibility to a flat tetrahedronal crystal form obtained as mentioned above, that is cubical crystals etc., were gathered, recrystallized, the flat tetrahedronal crystals and cubical crystals etc. were separated, just the flat tetrahedronal crystals were gathered, and the remaining cubical crystals etc. were then again recrystallized. This operation was repeated 15 times. All the flat tetrahedronal crystals obtained in this way and the above-mentioned flat tetrahedronal crystals (that obtained before the 15 recrystallizations) were mixed and an elementary analysis was performed. The results are shown below:

| Cl: 60, | Na: 37, | Mg: 0.20, |
|---|---|---|
| Br: 0.05, | S: 0.5, | Ca: 0.05, |
| K: 0.05, | Sr: 0.01, | Al: 0.05, |
| Si: 0.5, | Zr: 0.01 | Others: 1.58. |

Further, the lattice constant of the flat tetrahedronal crystal was found by wide angle X-ray diffraction, whereupon the value of the lattice constant was $a = 5.6385$ ($\pm 0.0003$) angstroms.

In the above-mentioned wide-angle X-ray diffraction (diffractometer method), use is made of an X-ray generating apparatus [Rigaku Denki Model RU-200B (rotating cathode pair type); X-ray source = $CUK\alpha$, curved crystal monochrometer (graphite) used; output = 40 KV and 150 mA], a goniometer (Rigaku Denki Model 2155D; slit system = $1° - 0.15$ mm $- 1°$; detector: scintillation counter], and a count recording apparatus [Rigaku Denki Model RAD-B]. Further, the reversion of the Miller indexes of the peaks by $K\alpha_1$ and $K\alpha_2$ was performed based on a JCPDAS card (5-0628). Using the reverted Miller index value and the values of the diffraction angles of the peaks, the lattice constant was determined by the minimum square method assuming the crystal system was cubic. However, at this time, the ratios of weight with the minimum square method of the diffraction peaks by $K\alpha_1$ and $K\alpha_2$ respectively match the ratios of strength and are 2:1. Note that the lattice constant of NaCl (Halite) registered on the JCPDS card (5-0628) is $a = 5.6402$ angstroms.

EXAMPLE 2

Just the cubical crystals precipitated along with the flat tetrahedronal crystals in Example 1 were collected, and 0.1 g of the cubical sodium chloride crystals were dissolved in 2 g of water of 22° C. and allowed to stand at ordinary temperature one night. The flat tetrahedronal crystals of about 0.1 mm to 3 mm (length of one side a of bottom face) accounted for 15% of the crystals obtained.

EXAMPLE 3

One gram of a mixture of the flat tetrahedronal crystals and cubical crystals (unique crystal sodium chloride) prepared in Example 1 was placed in a beaker and diluted $10^6$ fold by distilled water. Next, ferric chloride ($FeCl_3.6H_2O$) was added to 24% w/v, the solution was stirred, then allowed to stand at ordinary temperature one night. The aqueous solution obtained in this way is referred to below as the stock solution.

EXAMPLE 4

The stock solution obtained in Example 3 was further diluted $10^9$ fold by distilled water and taken in a test tube, five small earthworms were placed in the same, then the test tube was sealed. The test tube was allowed to stand, giving no feed at all and maintaining the water temperature at 15° C. to 20° C. At the same time as this, similar tests were performed using tap water and distilled water. In the distilled water test, all the small earthworms died after two days from the start of the test. In the tap water test, all died after three days. As opposed to this, in the test of the dilution of the stock solution of Example 3, almost no change could be observed in the small earthworms even after one month.

EXAMPLE 5

The stock solution obtained in Example 3 was further diluted $10^9$ fold with distilled water and taken in a test tube. The stem portion of a rose for flower arrangement was immersed in the solution. Approximately 3 cm of the stem was cut off in the solution and immersed as it was for 20 minutes. After that, the stem portion was fully flushed with tap water, placed in a vase containing tap water, and allowed to stand indoors away from the sunlight.

Roses not immersed in the solution containing the stock solution of Example 3 showed abnormalities in the flowers on the fourth day. The leaves and stem both wilted on the sixth day. As opposed to this, the roses immersed in the above-mentioned solution showed abnormalities in the flowers on the 11th day and thereupon became unsuited for decorative use, but almost no change was observed in the leaves and stem, which remained normal until the 20th day.

The same test was performed for carnations, whereupon those not immersed in a solution containing the above-mentioned stock solution had wilted flowers on the 5th day and abnormalities appearing in the leaves on the 14th day, while those immersed in the solution containing the above-mentioned stock solution had flowers lasting until the 13th day and leaves and stems for which almost no abnormalities were observed even after one month.

EXAMPLE 6

The following aqueous solution sample was manufactured and diluted $10^9$ fold with distilled water, then the tests of Example 4 and Example 5 were performed under the same conditions. The results are shown below.

One gram of the flat tetrahedronal crystal prepared in Example 1 was taken into a beaker and diluted $10^6$ fold with distilled water. Next, ferric chloride ($FeCl_3.6H_2O$) was added to 24% w/v, the solution was stirred, then it was allowed to stand at ordinary temperature for one night. The aqueous solution obtained in this way is referred to as sample No. 1.

One gram of the cubical crystals (sodium chloride with convertibility to flat tetrahedronal crystal form) prepared in Example 1 was taken into a beaker and diluted $10^6$ fold with distilled water. Next, ferric chloride ($FeCl_3.6H_2O$) was added to 24% w/v, the solution was stirred, then it was allowed to stand at ordinary temperature for one night. The aqueous solution obtained in this way is referred to as sample No. 2.

One gram of nontreated sodium chloride was taken into a beaker and diluted $10^6$ fold with distilled water. The aqueous solution thus obtained is referred to below as sample No. 3.

One gram of nontreated sodium chloride was taken into a beaker and diluted $10^6$ fold with distilled water. Next, ferric chloride ($FeCl_3.6H_2O$) was added to 24% w/v, the solution was stirred, then it was allowed to stand at ordinary temperature for one night. The aqueous solution obtained in this way is referred to as sample No. 4.

One gram of the flat tetrahedronal crystal prepared in Example 1 was taken into a beaker and diluted $10^6$ fold with distilled water. The aqueous solution obtained in this way is referred to as sample No. 5.

One gram of the sodium chloride with convertibility to flat tetrahedronal crystal prepared in Example 1 was taken into a beaker and diluted $10^6$ fold with distilled water. The aqueous solution obtained in this way is referred to as sample No. 6.

TABLE 1

| Sample No. | Small earthworm test (same as Example 4) | Cut rose test (same as Example 5) | Cut carnation test (same as Example 5) |
| --- | --- | --- | --- |
| 1 | Almost no changes observed in small earth worm even after elapse of one month | Rose showed abnormality in flower on 11th day, making it unsuited for use as decoration, but almost no changes were observed in leaves and stem, which remained normal until 20th day | Flower lasted until 13th day, while almost no abnormalities were recognized in leaves and stem even after elapse of one month. |
| 2 | Same as above | Same as above | Same as above |
| 3 | All small earthworms died after two days from the start of the test. | Rose showed abnormalities in flower on 4th day and had leaves and stem which wilted on 6th day. | Flower wilted on 5th day and abnormalities appeared in leaves on 17th day. |
| 4 | All died after 3rd day. | Rose showed abnormalities in flower on 4th day and had | Flower wilted on 5th day and abnormalities |

TABLE 1-continued

| Sample No. | Small earthworm test (same as Example 4) | Cut rose test (same as Example 5) | Cut carnation test (same as Example 5) |
|---|---|---|---|
|  |  | leaves and stem which wilted on 7th day. | appeared in leaves on 17th day. |
| 5 | All small earthworms died after two days from the start of the test. | Rose showed abnormalities in flower on 5th day and had leaves and stem which wilted on 8th day. | Flower wilted on 6th day and abnormalities appeared in leaves on 18th day. |
| 6 | Same as above. | Rose showed abnormalities in flower on 4th day and had leaves and stem which wilted on 7th day. | Flower wilted on 6th day and abnormalities appeared in leaves on 18th day. |

EXAMPLE 7

The stock solution obtained in Example 3 (below, referred to as sample No. 7) and the sample Nos. 1 to 6 shown in Example 6 were further diluted $10^6$ fold with distilled water and a coal (powdered coal) test, more specifically, a combustion test of the volatile components in coal, was performed. Four ml of the above seven types of aqueous solutions were placed in evaporation dishes, 4 g portions of coal (powdered coal) were added therein and stirred, and the solutions were allowed to stand overnight (until seven types of aqueous solutions were completely absorbed by coal). The evaporation dishes were heated from the top and bottom for five minutes for combustion, then the weights of the residues were measured. Using the results, the amounts of reduction in 4 g of coal were found. The amounts of reduction, shown in percent by weight, were as follows:

They were 36.6% for sample No. 7, 36.3% for No. 1, 36.1% for No. 2, 14.9% for No. 3, 14.0% for No. 4, 15.2% for No. 5, and 15.2% for No. 6. Further, the composition of the coal used in this example was found to be 1.8% moisture (amount of reduction upon heating at 107° C. for 60 minutes), 28.5% volatile components (amount of reduction upon heating at 150° C. for seven minutes), 14.8% ash (residue after heating at 750° C. for three minutes), 54.9% fixed carbon (remainder after elimination of moisture, volatile components, and ash).

Based on the above results, for example Nos. 3 to 6, only about half of the volatile components were combusted, but for example No. 1, No. 2, and No. 7, the volatile components and even part of the fixed carbon were combusted, it is clear. From these results, the aqueous solution of the present invention would contribute to the combustion efficiency of energy if used for slurrization of coal.

EXAMPLE 8

The stock solution obtained in Example 3 was further diluted $10^6$ fold with distilled water. Separately, 203 ml of seawater, 3 g of calcium hydroxide, and 2.5 ml of a rust preventative (Fujisawa Yakuhin Kogyo, trade name Palic C) were placed in a beaker and given the above-mentioned diluted aqueous solution to make the full volume 500 ml. Based on measurement of the natural electrode potential, a polished surface iron reinforcement bar and standard electrode were placed in a beaker. At first, the natural electrode potential was 330 mV. After 15 hours, it became 260 mV and then did not change for the subsequent two days.

On the other hand, 203 ml of seawater and 3 grams of calcium hydroxide were placed in a separate beaker, distilled water was added to make 480 ml, the amount of rust preventative (same as above) was changed variously, and distilled water was added to result in 500 ml.

When the amount of the rust preventative was 10 ml, the natural electrode potential was 258 mV. From this, it is understood that if use is made of the aqueous solution of the present invention instead of water, the amount of rust preventative used can be reduced to $\frac{1}{4}$ or less.

EXAMPLE 9

The sodium chloride of a flat tetrahedronal crystal obtained in Example 2 was added to an emulsion dispersion cream composition containing vitamin A acid. This was used as sample No. 8. The composition was as shown below:

|  |  | (% wt) |
|---|---|---|
| 1. | Squalane | 7.00 |
| 2. | Stearic acid | 3.00 |
| 3. | Cetanol | 4.00 |
| 4. | Self-emulsifying type monoglyceride | 2.00 |
| 5. | Cetyl ether | 2.00 |
| 6. | Propylene glycol | 5.00 |
| 7. | Glycerine | 5.00 |
| 8. | Phenoxyethanol | 1.00 |
| 9. | Vitamin A acid | 0.05 |
| 10. | Distilled water | 70.65 |
| 11. | Flat tetrahedronal crystal sodium chloride | 0.3 |

Note that the components 1 to 8 of the above-mentioned cream formulation are basic components normally used in this type of cream formulation. Even when other normally used components known to persons skilled in the art are formulated in, the flat tetrahedronal crystal sodium chloride according to the present invention displays the same effects as mentioned below.

Instead of flat tetrahedronal crystal sodium chloride, in sample No. 8, nontreated sodium chloride was added. This cream formulation was used as sample No. 9. Further, instead.. of the flat tetrahedronal crystal sodium chloride, in sample No. 8, 0.3% by weight of distilled water was added. This cream formulation was used as sample No. 10. The cream formulations of sample No. 8, No. 9, and No. 10 were applied to the head portions of 10 panelers. The application was performed twice a day with about 50 mg of the formulations and continued for 30 days.

With the cream formulation of sample No. 9, red spots occurred in two persons three days after the application, one on the fourth day, and one on the fifth day. With the cream formulation of sample No. 10, red spots occurred in three persons three days after the application and one on the fourth day. As opposed to this, with the cream formulation of sample No. 8, there were no persons suffering from red spots even after the elapse of 14 days from the application. Further, even in an accelerated ageing test (40° C. for six months), the cream formulation of sample No. 8 did not separate and remained stable.

EXAMPLE 10

The sodium chloride of a flat tetrahedronal crystal obtained in Example 2 was added to an emulsion dispersion cream composition containing vitamin A acid. This was used as sample No. 11. The composition is as shown below:

|  | (% wt) |
|---|---|
| 1. Squalane | 7.00 |
| 2. Stearic acid | 3.00 |
| 3. Cetanol | 4.00 |
| 4. Self-emulsifying monoglyceride | 2.00 |
| 5. Cetyl ether | 2.00 |
| 6. Propylene glycol | 5.00 |
| 7. Glycerine | 5.00 |
| 8. Phenoxyethanol | 1.00 |
| 9. Vitamin A acid | 0.05 |
| 10. Distilled water | 69.95 |
| 11. Flat tetrahedronal crystal sodium chloride | 1.00 |

Instead of flat tetrahedronal crystal sodium chloride, in sample No. 11, nontreated sodium chloride was added. This cream formulation was used as sample No. 12. Further, instead of the flat tetrahedronal crystal sodium chloride, in sample No. 11, 1.0% by weight of distilled water was added. This cream formulation was used as sample No. 13. The cream formulations of sample No. 11, No. 12, and No. 13 were applied to the head portions of 10 panelers. The same application test was performed as in Example 9.

Regarding the cream formulation of sample No. 12, red spots were caused in two persons on the third day after application, one on the fourth day, and one on the fifth day. Regarding the cream formulation of sample No. 13, red spots were caused in three persons on the third day after application and one on the fourth day. As opposed to this, regarding the cream formulation of sample No. 11, none of the persons suffered from red spots even after elapse of 14 days from the application. Further, even in the accelerated ageing test (40° C. for six months), the cream formulation of sample No. 11 did not separate and remained stable.

In the above way, the flat tetrahedronal crystal sodium chloride has the effect of suppressing secondary effects and the effect of improving chemical stability in a cream formulation including vitamin A acid, it was learned.

I claim:

1. Sodium chloride in a flat tetrahedronal crystal form.

2. Sodium chloride as claimed in claim 1, wherein a ratio of a length a of one side of an equilateral triangle base of the flat tetrahedronal crystal to a shortest height h of the flat tetrahexadronal crystal (a:h) is 1:0.8 to 50:1.

3. A method of preserving a cut flower, comprising using a cut flower preserving effective amount of an aqueous solution prepared from sodium chloride selected from the group consisting of crystals of sodium chloride in a flat tetrahedronal crystal form and crystals of sodium chloride capable of being converted to a flat tetrahedronal crystal form by recrystallization, said aqueous solution further containing iron chloride.

4. A method as claimed in claim 3, wherein the amount of iron chloride is 2500 to $25 \times 10^8$ parts by weight based upon 1 part by weight of sodium chloride and the amount of water is $10^6$ to $10^{20}$ parts by weight based upon 1 part by weight of the total weight of sodium chloride and iron chloride.

* * * * *

UNITED STATES PATENT AND TRADEMARK OFFICE
CERTIFICATE OF CORRECTION

PATENT NO. : 5,021,079

DATED : June 4, 1991

INVENTOR(S) : Nakane

It is certified that error appears in the above-identified patent and that said Letters Patent is hereby corrected as shown below:

On the title page, item [73], "Techno", should read --Tecno--.

Signed and Sealed this

Sixth Day of October, 1992

Attest:

DOUGLAS B. COMER

*Attesting Officer*   Acting Commissioner of Patents and Trademarks